United States Patent
Ishikawa et al.

(10) Patent No.: US 10,131,869 B2
(45) Date of Patent: Nov. 20, 2018

(54) **SPECIES OF *PLEUROTUS* SP. AND METHOD FOR PRODUCING SAME**

(71) Applicant: HOKUTO CORPORATION, Nagano (JP)

(72) Inventors: Mariko Ishikawa, Nagano (JP); Satoshi Inatomi, Nagano (JP); Kenji Ouchi, Nagano (JP); Takeshi Oku, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 817 days.

(21) Appl. No.: 14/418,877

(22) PCT Filed: Dec. 10, 2012

(86) PCT No.: PCT/JP2012/007868
§ 371 (c)(1),
(2) Date: May 14, 2015

(87) PCT Pub. No.: WO2014/020653
PCT Pub. Date: Feb. 6, 2014

(65) Prior Publication Data
US 2015/0296735 A1 Oct. 22, 2015

(30) Foreign Application Priority Data
Jul. 31, 2012 (JP) ................................. 2012-169032

(51) Int. Cl.
*C12N 1/14* (2006.01)
*A01H 1/02* (2006.01)
*A01H 15/00* (2006.01)

(52) U.S. Cl.
CPC ............. *C12N 1/14* (2013.01); *A01H 1/02* (2013.01); *A01H 15/00* (2013.01)

(58) Field of Classification Search
None
See application file for complete search history.

(56) References Cited

PUBLICATIONS

Tagavi et al 2016 Russian Agricultural Sciences 42(3-4): 230-235.*
Zhao et al 2016 Nature Scientific Reports No. 6, 33066, 9 pages.*
Bao et al 2004, Journal of Wood Science 50: 162-168.*
Rodriguez Estrada et al 2010 Fungal Biology 114: 421-428.*
Katsuhiko Babasaki et al., "Hiratake Zoku Kinoko 'Bai-Ling-Gu' no Bunruigakuteki Ichi o Akiraka ni shimasita", Forestry and Forest Products Research Institute Dai 2 ki Chuki Keikaku Seikashu, 2011, pp. 38 to 39.
Koichi Sugita et al., "Interspecific Hybridization of Basidiomycetous Fung Genus *Pleurotus* t by Protoplast Fusion", Nippon Hakko Kogakukai Taikai Koen Yoshishu, 1987, p. 76.
Fukushima-ken Ringyou Shikenjou Keikyuu Houkoku, 1994, No. 27, p. 121-146.
Fukushima-ken Ringyou Shikenjou Keikyuu Houkoku, 1997, No. 30, p. 61-78.
Yasumi Akamatsu, "Indentification of Isolates of *Pleurotus* species from Fukui Prefecture with Compatibilities in Pairing Experiments", Journal of Wood Science, 1998, vol. 44, No. 2, pp. 140 to 144.

\* cited by examiner

*Primary Examiner* — David H Kruse
(74) *Attorney, Agent, or Firm* — Konomi Takeshita

(57) ABSTRACT

The object of the invention is to provide a method for developing a novel species by means of interspecific crossbreeding among *P. eryngii* (DC.:Fr.) Quel., *P. eryngii* (DC.:Fr.) Quel. var. *elaeoselini*, *P. eryngii* (DC.:Fr.) Quel. var. *tuoliensis* C. J. Mou and *P. nebrodensis* (DC.:Fr.) Quel., which are not native in Japan, and *P. ostreatus* (Jacq.: Fr.) Kummer, which is native in Japan and the novel species obtained by the method and is also to provide a novel species of *Pleurotus* spp. carrying both a *P. eryngii* (DC.:Fr.) Quel. gene and a *P. ostreatus* (Jacq.: Fr.) Kummer gene by crossbreeding *P. ostreatus* (Jacq.: Fr.) Kummer with *P. eryngii* (DC.:Fr.) Quel. var. *tuoliensis* C. J. Mou, *P. nebrodensis* (DC.:Fr.) Quel. or *P. eryngii* (DC.:Fr.) Quel. var. *ferulae* Lanzi, thereby obtaining a strain capable of further crossbreeding with *P. eryngii* (DC.:Fr.) Quel., *P. eryngii* (DC.:Fr.) Quel. var. *elaeoselini* or the like.

2 Claims, 1 Drawing Sheet
Specification includes a Sequence Listing.

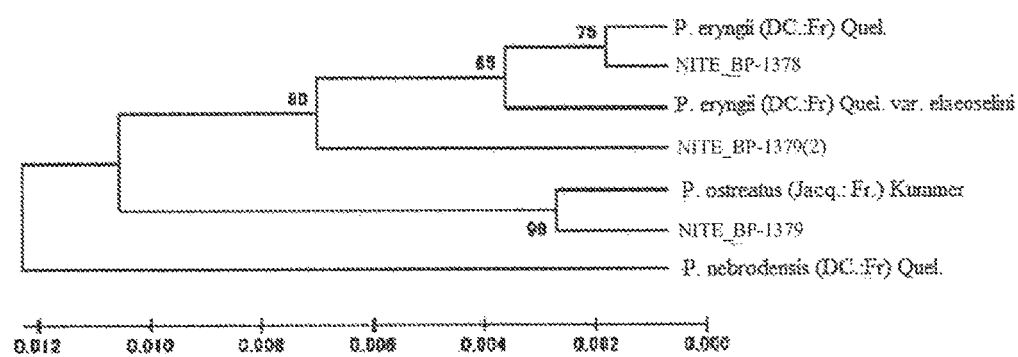

SPECIES OF *PLEUROTUS* SP. AND METHOD FOR PRODUCING SAME

CROSS REFERENCE TO RELATED APPLICATIONS

This application claims priority under 35 U.S.C. 119 based upon Japanese Patent Application Serial No. 2006-273382, filed on Oct. 4, 2006 and PCT Intl. Pat. Appl. No. PCT/JP2012/007868, filed on Dec. 10, 2012; the contents of each of which is specifically incorporated herein in its entirety by express reference thereto.

INCORPORATION OF SEQUENCE LISTING

The sequence listing for this application has been submitted in accordance with 37 CFR § 1.821 and 37 CFR § 1.52(e) as a text file entitled "Y14S005PCT-US Seq List revised.txt" created on Dec. 15, 2017, 6 kb. Applicants hereby incorporate by reference the sequence listing provided in the text file as both the paper copy and the computer-readable form (CRF) of the sequence listing required by 37 CFR § 1.821. The information in the electronic format of the sequence listing is incorporated herein by reference in its entirety.

FIELD OF THE INVENTION

The present invention relates to a method for developing a novel species using a plurality of *Pleurotus* spp. and the novel species.

BACKGROUND OF THE INVENTION

As *Pleurotus* spp. native in Japan (hereinafter referred to as domestic varieties), *P. ostreatus* (Jacq.: Fr.) Kummer (SEQ ID NO. 1), *P. salmoneostramineus* L. Vass., *P. cornucopiae* (Paulet) Rolland var. *citrinopileatus* (Sing.) Ohira, *P. abalonus* Y. H. Han, K. M. Chen & S. Cheng and *P. pulmonarius* (Fr.) Quel., etc. have conventionally been known. Among these, *P. ostreatus* (Jacq.: Fr.) Kummer has been enjoyed as a minor forest product, but the disadvantage is that caps are liable to be broken in the course of distribution and cooking, and therefore the amount of domestic production has been decreasing since about 1989.

On the other hand, as *Pleurotus* spp. that are not native in Japan (hereinafter referred to as foreign varieties), *P. eryngii* (DC.:Fr.) Quel. (SEQ ID NO. 3), *P. nebrodensis* (DC.:Fr.) Quel. (SEQ ID NO. 2), *P. eryngii* (DC.:Fr.) Quel. var. *ferulae* Lanzi, *P. eryngii* (DC.:Fr.) Quel. var. *elaeoselini* (SEQ ID NO. 4), *P. eryngii* (DC.:Fr.) Quel. var. *tuoliensis* C. J. Mou, etc. have been known (Non-Patent Literature 1, Non-Patent Literature 2), and *P. eryngii* (DC.:Fr.) Quel. have been produced and sold in Japan since about 1995, and *P. eryngii* (DC.:Fr.) Quel. var. *tuoliensis* C. J. Mou, etc. also came to be sold several years later. Among these, *P. eryngii* (DC.:Fr.) Quel. is a high-demand commodity, and the amount of domestic production has been increasing. *P. eryngii* (DC.:Fr.) Quel. var. *tuoliensis* C. J. Mou, etc. that got into the business later have not expanded the market yet as a new market because, among others, they are similar to *P. eryngii* (DC.:Fr.) Quel., and therefore there is a strong need to develop novel varieties.

Incidentally, in the *Pleurotus* spp., the crossbreeding among foreign varieties has recently been confirmed (Non-Patent Literature 2). However, there is no example of crossbreeding a domestic variety with a foreign variety, and in regard of the genealogical tree, it is believed that those species cannot be crossbred because they can be classified into different groups (Non-Patent Literature 2, Non-Patent Literature 3). Accordingly, no novel species having both characteristics of a domestic variety and a foreign variety has been developed yet (Patent Literatures 1-6).

PRIOR ART LITERATURE

Patent Literature

Patent Literature 1: Japanese Patent Application Kokai Publication No. 2011-109941
Patent Literature 2: Japanese Patent Application Kokai Publication No. 2011-110046
Patent Literature 3: Japanese Patent Application Kokai Publication No. 2009-22218
Patent Literature 4: Japanese Patent Application Kokai Publication No. 2008-104380
Patent Literature 5: Japanese Patent Application Kokai Publication No. 2007-37455
Patent Literature 6: Japanese Patent Application Kokai Publication No. 2006-67930

Non-Patent Literature

Non-Patent Literature 1: G. Venturella et al. *Pleurotus eryngii* var. *elaeoselini* var. nov. from Sicily Mycotaxon, 76, 419-427 (2000).
Non-Patent Literature 2: G. Kawai et al. Taxonomic position of a Chinese *Pleurotus* "Bai-Ling-Gu": it belongs to *Pleurotus eryngii* (DC.:Fr.) Quel. and evolved independently in China, Mycoscience, 49, 75-87 (2008).
Non-Patent Literature 3: D. Bao et al. The biological species of oyster mushroom (*Pleurotus* spp.) from Asia based on mating compability tests, J Wood Sci, 50, 162-168 (2004).

SUMMARY OF THE INVENTION

The problem that the present invention is to solve is to find a combination that can be crossbred between a domestic variety and a foreign variety and provide a novel species having both characteristics of a domestic variety and a foreign variety (an interspecific hybrid) and a technique relating to a method for developing the interspecific hybrid.

As a result of intensive studies in order to solve the abovementioned problem, the present inventors succeeded in crossbreeding *P. ostreatus* (Jacq.: Fr.) Kummer with a foreign variety such as *P. eryngii* (DC.:Fr.) Quel. var. *tuoliensis* C. J. Mou, *P. nebrodensis* (DC.:Fr.) Quel. or *P. eryngii* (DC.:Fr.) Quel. var. *ferulae* Lanzi and provide a method capable of developing a wide variety of interspecific hybrids by crossbreeding the crossbreed with *P. eryngii* (DC.:Fr.) Quel., *P. eryngii* (DC.:Fr.) Quel. var. *elaeoselini* or the like and novel species (interspecific hybrids) obtained by the method.

In other words, the first embodiment of the invention is a method for developing an interspecific hybrid, comprising crossbreeding *P. ostreatus* (Jacq.: Fr.) Kummer, a domestic variety, with a foreign variety of *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi.

The second embodiment of the invention is an interspecific hybrid obtained by the method according to the first embodiment of the invention.

The third embodiment of the invention is a method for developing an interspecific hybrid of *Pleurotus* spp., comprising crossbreeding the interspecific hybrid according to the second embodiment of the invention with either *P. eryngii* (DC.:Fr.) Quel. or *P. eryngii* (DC.:Fr.) Quel. var. *elaeoselini*.

The fourth embodiment of the invention is an interspecific hybrid of *Pleurotus* spp. obtained by the method according to the third embodiment of the invention.

The fifthe embodiment of the invention is a method for developing an interspecific hybrid of *Pleurotus* spp. between *P. ostreatus* (Jacq.: Fr.) Kummer, a domestic variety, and an interspecific hybrid of foreign varieties, comprising obtaining a crossbreed of any two varieties from among *P. nebrodensis* (DC.:Fr.) Quel., *P. eryngii* (DC.:Fr.) Quel. var. *tuoliensis* C. J. Mou, *P. eryngii* (DC.:Fr.) Quel. var. *ferulae* Lanzi, *P. eryngii* (DC.:Fr.) Quel. and *P. eryngii* (DC.:Fr.) Quel. var. *elaeoselini* in such a manner that one parent is *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi, and crossbreeding the crossbreed with *P. ostreatus* (Jacq.: Fr.) Kummer.

The sixth embodiment of the invention is an interspecific hybrid of *Pleurotus* spp. obtained by the method according to the fifth embodiment of the invention.

The seventh embodiment of the invention is the method for developing an interspecific hybrid of *Pleurotus* spp. according to any one of the first, third and fifth embodiments of the invention, wherein a crossbreed obtained by crossbreeding two varieties from among *P. nebrodensis* (DC.:Fr.) Quel., *P. eryngii* (DC.:Fr.) Quel. var. *tuoliensis* C. J. Mou and *P. eryngii* (DC.:Fr.) Quel. var. *ferulae* Lanzi is used in place of *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi.

The eighth embodiment of the invention is the method for developing an interspecific hybrid of *Pleurotus* spp. according to any one of the third, fifth and seventh embodiments of the invention, wherein a crossbreed obtained by crossbreeding *P. eryngii* (DC.:Fr.) Quel. with *P. eryngii* (DC.:Fr.) Quel. var. *elaeoselini* is used in place of *P. eryngii* (DC.:Fr.) Quel. or *P. eryngii* (DC.:Fr.) Quel. var. *elaeoselini*.

The ninth embodiment of the invention is an interspecific hybrid obtained by the method according to the seventh and eighth embodiments of the invention between *P. ostreatus* (Jacq.: Fr.) Kummer, a domestic variety, and a foreign variety.

The tenth embodiment of the invention is a cultivation method for generating a mushroom by inoculating a mushroom cultivation medium with an interspecific hybrid of *Pleurotus* spp. between *P. ostreatus* (Jacq.: Fr.) Kummer, a domestic variety, and a foreign variety.

The eleventh embodiment of the invention is Deposit No. NITE BP-1378 or NITE BP-1379, which is a novel species of *Pleurotus* spp., obtained by the interspecific crossbreeding between *P. ostreatus* (Jacq.: Fr.) Kummer, a domestic variety, and a foreign variety.

The twelfth embodiment of the invention is a method for cultivating Deposit No. NITE BP-1378 or NITE BP-1379, which is a novel variety of *Pleurotus* spp., obtained by the interspecific crossbreeding between *P. ostreatus* (Jacq.: Fr.) Kummer, a domestic variety, and a foreign variety in a mushroom cultivation medium.

Effect of the Invention

The present invention has made it possible to produce an interspecific hybrid between *P. ostreatus* (Jacq.: Fr.) Kummer, a domestic variety, and a foreign variety. Accordingly, it has been made possible to produce a novel species carrying both a *P. ostreatus* (Jacq.: Fr.) Kummer gene and a *P. eryngii* (DC.:Fr.) Quel. gene, which is unheard of up to now. Specifically, the following describes each effect of the present invention.

The first and second embodiments of the invention enable to crossbreed *P. ostreatus* (Jacq.: Fr.) Kummer, a domestic variety, with *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi, which is a foreign variety, so that an interspecific hybrid between a domestic variety and a foreign variety can be obtained and furthermore enable to crossbreed a foreign variety, which could not be crossbred with *P. ostreatus* (Jacq.: Fr.) Kummer, with a variety carrying a *P. ostreatus* (Jacq.: Fr.) Kummer gene. Novel species that did not conventionally exist can make a contribution to pioneering a new market.

The third and fourth embodiments of the invention enable to crossbreed *P. eryngii* (DC.:Fr.) Quel. or *P. eryngii* (DC.:Fr.) Quel. var. *elaeoselini*, which is a foreign variety and could not be crossbred with *P. ostreatus* (Jacq.: Fr.) Kummer, a domestic variety, and, therefore, enable to introduce traits of popular *P. eryngii* (DC.:Fr.) Quel. into *P. ostreatus* (Jacq.: Fr.) Kummer or incorporate characteristic traits of *P. ostreatus* (Jacq.: Fr.) Kummer into *P. eryngii* (DC.:Fr.) Quel. More specifically, the effect is such that it is possible to develop mushrooms whose external appearance is similar to *P. ostreatus* (Jacq.: Fr.) Kummer but which have the taste of *P. eryngii* (DC.:Fr.) Quel. or mushrooms whose cap color is similar to *P. ostreatus* (Jacq.: Fr.) Kummer but which has a thick stem as in *P. eryngii* (DC.:Fr.) Quel. in terms of shape.

The fifth to ninth embodiments of the invention enable, at the time of crossbreeding *P. ostreatus* (Jacq.: Fr.) Kummer, a domestic variety, with a foreign variety, to produce an interspecific hybrid of foreign varieties in a pattern capable of crossbreeding among foreign varieties and crossbreed the produced interspecific hybrid of foreign varieties with *P. ostreatus* (Jacq.: Fr.) Kummer, a domestic variety, to thereby develop interspecific hybrids of more variations. By way of example, the effect is such that it is possible to contain nutritional components unique to each variety used as a hybrid parent and that it is also possible to develop varieties having colors that could not be developed by *P. ostreatus* (Jacq.: Fr.) Kummer or by crossbreeding among various foreign varieties.

The tenth embodiment of the invention enables to produce a large amount of a novel species obtained by crossbreeding *P. ostreatus* (Jacq.: Fr.) Kummer, a domestic variety, with a foreign variety by inoculating a mushroom cultivation medium therewith. Since large-scale production is enabled, a new market can be developed so that economic expansion can also be expected.

The eleventh and twelfth embodiments of the invention provide a novel species obtained by crossbreeding a domestic variety with a foreign variety. An interspecific hybrid can be produced without crossbreeding.

BRIEF DESCRIPTION OF THE DRAWINGS

The FIGURE is a view showing the genealogical relationship among a domestic variety, foreign varieties and Deposit No. NITE BP-1378 and NITE BP-1379 obtained by the present invention by the UPGMA method.

DETAILED DESCRIPTION OF THE INVENTION

In regard of foreign varieties necessary to implement the present invention, *P. eryngii* (DC.:Fr.) Quel., *P. eryngii*

(DC.:Fr.) Quel. var. *tuoliensis* C. J. Mou and *P. eryngii* (DC.:Fr.) Quel. var. *ferulae* Lanzi are on the market and, therefore, are easily available. On the other hand, *P. eryngii* (DC.:Fr.) Quel. var. *elaeoselini* and *P. nebrodensis* (DC.:Fr.) Quel. are hardly available in Japan but can be obtained from strain collection institutes or imported from the European market (e.g., Italy). Furthermore, care is needed about *P. eryngii* (DC.:Fr.) Quel. var. *tuoliensis* C. J. Mou at the time of acquisition because it is frequently confused with *P. nebrodensis* (DC.:Fr.) Quel.

In the present invention, an interspecific hybrid can be obtained by crossbreeding *P. ostreatus* (Jacq.: Fr.) Kummer, a domestic variety, from among *Pleurotus* spp. with a foreign variety such as *P. eryngii* (DC.:Fr.) Quel. var. *tuoliensis* C. J. Mou, *P. nebrodensis* (DC.:Fr.) Quel. or *P. eryngii* (DC.:Fr.) Quel. var. *ferulae* Lanzi. Then, by further using and crossbreeding the abovementioned interspecific hybrid with another foreign variety, it is possible to obtain an interspecific hybrid with a foreign variety such as *P. eryngii* (DC.:Fr.) Quel. that could not be crossbred with *P. ostreatus* (Jacq.: Fr.) Kummer.

Moreover, the present invention can achieve the purpose of producing a novel species of *Pleurotus* spp. having diversified traits by producing a novel species carrying the gene of *P. ostreatus* (Jacq.: Fr.) Kummer, a domestic variety, and a foreign variety gene, but in order to achieve the purpose, in the process of developing a foreign variety and an interspecific hybrid, it is necessary to perform crossbreeding at least once, which is capable of achieving the effect obtained by crossbreeding *P. ostreatus* (Jacq.: Fr.) Kummer, a domestic variety, with *P. eryngii* (DC.:Fr.) Quel. var. *tuoliensis* C. J. Mou, *P. nebrodensis* (DC.:Fr.) Quel. or *P. eryngii* (DC.:Fr.) Quel. var. *ferulae* Lanzi, which is a foreign variety, i.e., the effect equivalent to the ability of the interspecific hybrid in crossbreeding with *P. eryngii* (DC.: Fr.) Quel., etc.

By way of example, *P. nebrodensis* (DC.:Fr.) Quel. may be crossbred with *P. eryngii* (DC.:Fr.) Quel. var. *tuoliensis* C. J. Mou and then the crossbreed may be crossbred with *P. ostreatus* (Jacq.: Fr.) Kummer, or *P. nebrodensis* (DC.:Fr.) Quel. may be crossbred with *P. eryngii* (DC.:Fr.) Quel. and then the crossbreed may be crossbred with *P. ostreatus* (Jacq.: Fr.) Kummer. Alternatively, *P. nebrodensis* (DC.:Fr.) Quel. may be crossbred with *P. eryngii* (DC.:Fr.) Quel. var. *tuoliensis* C. J. Mou to obtain a crossbreed, the crossbreed may be crossbred with *P. eryngii* (DC.:Fr.) Quel. to further obtain a crossbreed, and then the crossbreed may be crossbred with *P. ostreatus* (Jacq.: Fr.) Kummer Crossbreeding can be repeated any number of times in a combination that enables crossbreeding before crossbreeding *P. ostreatus* (Jacq.: Fr.) Kummer with *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi, or crossbreeding can be repeated any number of times in a combination that enables crossbreeding after crossbreeding *P. ostreatus* (Jacq.: Fr.) Kummer with *P. nebrodensis* (DC.:Fr.) Quel., *P. eryngii* (DC.:Fr.) Quel. var. *tuoliensis* C. J. Mou or *P. eryngii* (DC.:Fr.) Quel. var. *ferulae* Lanzi.

An interspecific hybrid between *P. ostreatus* (Jacq.: Fr.) Kummer and a foreign variety can be produced using an ordinary crossbreeding method in the field of breeding techniques. In other words, the following method is used. Single spore isolation is performed by dropping spores from a parent mushroom, and a hypha is germinated from a single spore on an agar medium to obtain a monokaryotic hypha. Similarly, a monokaryotic hypha is obtained from another parent mushroom, and both monokaryotic hyphae are cultured on an agar medium by a dual culture. As the culture progresses, a crossbred hypha forms a clump. In other words, a crossbreed can be obtained by isolating a hypha in which a clump is observed. In this case, as the agar medium, an agar medium that can be used in culturing mushroom hyphae may be used including a potato dextrose agar medium.

Although a description of a crossbreeding method was described above, it is not that a crossbreeding method must be used, but other biotechnologies can be used including cell fusion and gene transfer.

In regard of the method for cultivating a produced interspecific hybrid, it can be cultivated using the prior art used for cultivating mushrooms of *Pleurotus* spp. In other words, a cultivation method used in *P. ostreatus* (Jacq.: Fr.) Kummer, *P. eryngii* (DC.:Fr.) Quel. and *P. eryngii* (DC.:Fr.) Quel. var. *tuoliensis* C. J. Mou can be applied.

In regard of the medium for cultivating interspecific hybrid mushrooms, a wide variety of grasses and trees can be used as medium materials including sawdust, corn cobs, cotton hulls, coconut husks, rice straws, beat pulps, soybean skins, soybean meals, corn grits, wheat bran, rice bran, barley, wheat, barley brans, oats, chaffs, corn bran, corn meals, corn fibers, corn hulls, milos, rapeseed cake, soybean oil cake, sesame oil cake, coffee cake, beans such as bagasse and tapioca, grains and root crops. In addition, refuse and lees produced in food processing can also be used including bean-curd refuse, shochu distillery by-products and brewer's grain. At the time of selecting medium materials, a medium used for *P. ostreatus* (Jacq.: Fr.) Kummer, *P. eryngii* (DC.: Fr.) Quel. and *P. eryngii* (DC.:Fr.) Quel. var. *tuoliensis* C. J. Mou can basically be used, but there are cases when a design needs to be changed more or less in synch with the characteristics of interspecific hybrids within the range of ordinary knowledge in the technical field of mushroom cultivation.

The containers used for cultivating interspecific hybrid mushrooms according to the present invention can be mushroom cultivation bottles, but it is also possible to cultivate mushrooms in mushroom cultivation bags. Since the use of a mushroom cultivation bottle facilitates mechanical work, a mushroom cultivation bottle is suitable for cultivating mushrooms industrially.

The method for cultivating interspecific hybrid mushrooms according to the present invention is a method in which after stirring medium materials optionally selected from the abovementioned medium materials, water is added such that moisture contents become about 60% to about 70%, (the mixture) is further stirred to adjust the medium, the medium is filled in a cultivation bottle, and after sterilization by heating, (the medium) is inoculated with an interspecific hybrid hypha according to the present invention, which is then cultured and subjected to germination treatment, and (the hypha) is further grown.

The standard management of culture is as follows. The temperature is managed at 20° C. to 23° C. and preferably at 22° C. The humidity is managed between 80% and 90%. The ventilation is managed such that the concentration of carbon dioxide gas in the culture chamber does not exceed 3000 ppm. The culture chamber should be kept dark.

The standard management of germination and growth is as follows. The temperature is managed at 14° C. to 15° C. The humidity is managed between 80% and 90%. The ventilation is managed such that the concentration of carbon dioxide gas in the germination chamber is not more than 750 ppm. About 100 lx of light is irradiated from a fluorescent lamp during the germination and growth.

Although the cultivation of *Pleurotus* spp. varieties can be managed well in the abovementioned environment, the number of days in culture, germination and growth varies depending on varieties. For example, the number of days in culture is 21 days in *P. ostreatus* (Jacq.: Fr.) Kummer, 28 days in *P. eryngii* (DC.:Fr.) Quel. and *P. eryngii* (DC.:Fr.) Quel. var. *elaeoselini*, 35 days in *P. eryngii* (DC.:Fr.) Quel. var. *tuoliensis* C. J. Mou and *P. eryngii* (DC.:Fr.) Quel. var. *ferulae* Lanzi, and 42 days in *P. nebrodensis* (DC.:Fr.) Quel. The number of days in germination and growth is 9 days in *P. ostreatus* (Jacq.: Fr.) Kummer, 14 days in *P. eryngii* (DC.:Fr.) Quel., *P. eryngii* (DC.:Fr.) Quel. var. *elaeoselini*, *P. eryngii* (DC.:Fr.) Quel. var. *tuoliensis* C. J. Mou and *P. eryngii* (DC.:Fr.) Quel. var. *ferulae* Lanzi, and 18 days in *P. nebrodensis* (DC.:Fr.) Quel.

In the case of interspecific hybrids, cultivation management varies depending on produced varieties, and cultivation management conditions vary depending on the cultivation conditions of parent varieties, and therefore it become easier to produce a plurality of interspecific hybrids and select an interspecific hybrid adapted for the growth environment of interest. For example, if a variety having a short cultivation cycle such as *P. ostreatus* (Jacq.: Fr.) Kummer is desired to be obtained, you should just set the number of days in culture, growth, etc. to a short period, cultivate mushrooms under the abovementioned standard management, examine whether or not traits of interest are provided, and if the interest has been achieved as a result of examination, select an interspecific hybrid that has achieved the interest.

Furthermore, we deposited two strains obtained by repeating crossbreeding several times using *P. ostreatus* (Jacq.: Fr.) Kummer, *P. nebrodensis* (DC.:Fr.) Quel., *P. eryngii* (DC.:Fr.) Quel. and *P. eryngii* (DC.:Fr.) Quel. var. *elaeoselini* to NITE (National Institute of Technology and Evaluation) Patent Microorganisms Depositary (NPMD), an independent administrative corporation, as strains that could be cultivated in a relatively short period. They have been deposited as NITE BP-1378 (SEQ ID NO. 5) and NITE BP-1379 (SEQ ID NO. 6).

The present invention is specifically described below with reference to examples, but the present invention is not restricted to the following examples at all as far as nothing departs from the spirit of the present invention.

Example 1

We performed single spore isolation to obtain monokaryotic hyphae from mushrooms of *Pleurotus* spp. i.e., *P. ostreatus* (Jacq.: Fr.) Kummer, *P. salmoneostramineus* L. Vass., *P. cornucopiae* (Paulet) Rolland var. *citrinopileatus* (Sing.) Ohira, *P. abalonus* Y. H. Han, K. M. Chen & S. Cheng and *P. pulmonarius* (Fr.) Quel., which are domestic varieties, and *P. eryngii* (DC.:Fr.) Quel. *P. nebrodensis* (DC.:Fr.) Quel., *P. eryngii* (DC.:Fr.) Quel. var. *ferulae* Lanzi, *P. eryngii* (DC.:Fr.) Quel. var. *elaeoselini* and *P. eryngii* (DC.:Fr.) Quel. var. *tuoliensis* C. J. Mou, which are foreign varieties. In each variety, monokaryotic hyphae were crossed with each other by a dual culture to observe whether or not mating is possible, and we then classified monokaryotic hyphae of the each variety into four mating types.

We selected eight strains of monokaryotic hyphae including two strains from each four mating types in the each variety and examined whether or not crossbreeding is possible by a dual culture in all combinations in which interspecific crossbreeding is possible. Table 1 shows the results. In Table 1, crossbred combinations are shown with +, and combinations in which no crossbreeding occurred are shown with −. Furthermore, the number of crossbred combinations is shown by percentage relative to all the combinations of respective interspecific crossbreeding as the crossing rate.

TABLE 1

|      | (1) | (2)  | (3)  | (4)  | (5)  | (6)  | (7)   | (8)   | (9)   | (10)  |
|------|-----|------|------|------|------|------|-------|-------|-------|-------|
| (1)  |     | 0.0% | 0.0% | 0.0% | 0.0% | 0.0% | 56.3% | 9.4%  | 0.0%  | 18.8% |
| (2)  | −   |      | 0.0% | 0.0% | 0.0% | 0.0% | 0.0%  | 0.0%  | 0.0%  | 0.0%  |
| (3)  | −   | −    |      | 0.0% | 0.0% | 0.0% | 0.0%  | 0.0%  | 0.0%  | 0.0%  |
| (4)  | −   | −    | −    |      | 0.0% | 0.0% | 0.0%  | 0.0%  | 0.0%  | 0.0%  |
| (5)  | −   | −    | −    | −    |      | 0.0% | 0.0%  | 0.0%  | 0.0%  | 0.0%  |
| (6)  | −   | −    | −    | −    | −    |      | 62.5% | 75.0% | 78.1% | 71.9% |
| (7)  | +   | −    | −    | −    | −    | +    |       | 54.7% | 31.3% | 50.0% |
| (8)  | +   | −    | −    | −    | −    | +    | +     |       | 70.3% | 62.5% |
| (9)  | −   | −    | −    | −    | −    | +    | +     | +     |       | 12.5% |
| (10) | +   | −    | −    | −    | −    | +    | +     | +     | +     |       |

(1): *P. ostreatus* (Jacq.: Fr.) Kummer,
(2): *P. salmoneostramineus* .L. Vass,
(3): *P. cornucopiae* (Paulet) Rolland var. *citrinopileatus* (Sing.) Ohira,
(4): *P. abalonus* Y. H. Han, K. M. Chen & S. Cheng,
(5): *P. pulmonarius* (Fr.) Quel.,
(6): *P. eryngii* (DC.: Fr.) Quel.,
(7): *P. nebrodensis* (DC.: Fr.) Quel.,
(8): *P. eryngii* (DC.: Fr.) Quel. var. *ferulae* Lanzi,
(9): *P. eryngii* (DC.: Fr.) Quel. var. *elaeoselini*,
(10): *P. eryngii* (DC.: Fr.) Quel. var. *tuoliensis* C. J. Mou.

Next, we conducted cultivation tests for crossbreeds between *P. nebrodensis* (DC.:Fr.) Quel. and *P. ostreatus* (Jacq.: Fr.) Kummer.

Example 2

We crossbred *P. nebrodensis* (DC.:Fr.) Quel. with *P. ostreatus* (Jacq.: Fr.) Kummer, optionally selected 90 strains, inoculated a mushroom cultivation medium with each hyphae of the 90 strains separately and examined the germination status of mushrooms. The mushrooms were cultivated as follows.

Method for Cultivating Mushrooms

We used a mushroom cultivation medium having the following combination in which *P. eryngii* (DC.:Fr.) Quel. could germinate well. We mixed corn cob, bean skin, wheat bran and rice bran at the ratio of 64:18:9:9 by weight ratio and added water after stirring to make a moisture content of 64%.

We filled a mushroom cultivation medium in an 850 mL mushroom cultivation bottle, depressed the medium while providing a hole, which penetrates from the upper surface to the bottom, toward the bottom from the center of the upper surface of the medium, and after attaching a cap to the neck of the bottle by fitting it together, sterilized at 118° C. for 15 minutes. After cooling the sterilized mushroom cultivation bottle to 20° C., we inoculated a hypha of a crossbreed between *P. nebrodensis* (DC.:Fr.) Quel. and *P. ostreatus* (Jacq.: Fr.) Kummer into the bottle. Subsequently, we cultured it at a temperature of 22° C. to 23° C. and a moisture of 80% to 90% for 21 days to 42 days, followed by scratching, subjected it to germination treatment at a temperature of 14° C. to 15° C. and a moisture of 80% to 90% for 6 days to 10 days, and after germination, made it grow at a temperature of 14° C. to 15° C. and a moisture of 80% to 90% for 3 days to 10 days before harvesting.

About the result of cultivating the crossbreeds between *P. nebrodensis* (DC.:Fr.) Quel. and *P. ostreatus* (Jacq.: Fr.) Kummer, Table 2 shows their agronomic characteristics and morphological characteristics.

(1) As to the number of days in culture, the standard number of days in culture for *P. ostreatus* (Jacq.: Fr.) Kummer was 21 days and the standard number of days in culture for *P. nebrodensis* (DC.:Fr.) Quel. was 42 days while that varied from 18 days to 36 days for the novel crossbreed.

(2) The number of days in growth (a period up to harvest from scratching treatment) varied from 9 days to 20 days, and we could obtain ones close to *P. ostreatus* (Jacq.: Fr.) Kummer, intermediate ones, ones close to *P. nebrodensis* (DC.:Fr.) Quel. and so on.

(3) In terms of morphological characteristics and tastes, we could also obtain various kinds of varieties such as ones having a shape and taste close to *P. ostreatus* (Jacq.: Fr.) Kummer, intermediate ones between *P. ostreatus* (Jacq.: Fr.) Kummer and *P. nebrodensis* (DC.:Fr.) Quel., and ones close to *P. nebrodensis* (DC.:Fr.) Quel.

As to the crossbreeding of a crossbreed between *P. ostreatus* (Jacq.: Fr.) Kummer and *P. nebrodensis* (DC.:Fr.) Quel. with *P. eryngii* (DC.:Fr.) Quel. or *P. eryngii* (DC.:Fr.) Quel. var. *elaeoselini*, we performed single spore isolation from each and then performed crossbreeding in a manner similar to that of Example 1. Table 3 shows the result of the crossbreeding. Numbers in Table 3 show the percentage of crossbreeding relative to all the combinations of respective interspecific crossbreeding. Since *P. ostreatus* (Jacq.: Fr.) Kummer was crossbred with *P. nebrodensis* (DC.:Fr.) Quel., we could crossbreed them with *P. eryngii* (DC.:Fr.) Quel. or *P. eryngii* (DC.:Fr.) Quel. var. *elaeoselini* to thereby produce a strain carrying genes of *P. eryngii* (DC.:Fr.) Quel. or *P. eryngii* (DC.:Fr.) Quel. var. *elaeoselini* and *P. ostreatus* (Jacq.: Fr.) Kummer.

TABLE 3

|  | *P. eryngii* (DC.:Fr.) Quel. | *P. eryngii* (DC.:Fr.) Quel. var. *elaeoselini* |
|---|---|---|
| Crossbreed between *P. ostreatus* (Jacq.:Fr.) Kummer and *P. nebrodensis* (DC.:Fr.) Quel. | 34.4% | 10.0% |

Example 4

We performed single spore isolation from a crossbreed between *P. ostreatus* (Jacq.: Fr.) Kummer and *P. nebrodensis* (DC.:Fr.) Quel, while also performing single spore isolation from a crossbreed between *P. eryngii* (DC.:Fr.) Quel. and *P. eryngii* (DC.:Fr.) Quel. var. *elaeoselini*, crossbred both monokaryotic hyphae by a dual culture, obtained 70 crossbred strains between the crossbreed between *P. ostreatus* (Jacq.: Fr.) Kummer and *P. nebrodensis* (DC.:Fr.) Quel and the crossbreed between *P. eryngii* (DC.:Fr.) Quel. and *P. eryngii* (DC.:Fr.) Quel. var. *elaeoselini* and cultivated them by a cultivation method similar to that of Example 2.

TABLE 2

|  |  |  | *P. ostreatus* (Jacq.:Fr.) Kummer | *P. nebrodensis* (DC.:Fr.) Quel. | Crossbreed between *P. ostreatus* (Jacq.: Fr.) Kummer and *P. nebrodensis* (DC.: Fr.) Quel. |
|---|---|---|---|---|---|
| Agronomic characteristics | Days in culture | | 21 days | 42 days | 18 days to 36 days |
| | Days in growth | | 9 days | 18 days | 9 days to 20 days |
| | Yielding ability (w/w) | | Yield 22.1% | Yield 17.6% | Yield 15.8% to 23.7% |
| Morphological characteristics | Cap | Shape | Concave type | Concave type | Funnel type, concave type, flat type |
| | | Color | Gray-brown | Light yellow white | White, light yellow white, gray-brown |
| | Stem | Shape | Thin and short | Thick in the middle | Thin and long, thin and short, thick in the middle |
| | | Color | White | Light yellow white | White, light yellow white |
| Taste and flavor | Taste | | Bitter | sweetness | Diversified including ones having bitterness, ones whose bitterness is mitigated and ones having chestnut-like sweetness. |
| | Food texture | | Soft and lack of crispiness | Crunchy and crispy | Diversified including ones close to *P. ostreatus* (Jacq.: Fr.) Kummer, ones close to *P. nebrodensis* (DC.:Fr.) Quel. and ones that can resemble neither of them. |

About the result of cultivating the crossbreeds between the crossbreed between *P. ostreatus* (Jacq.: Fr.) Kummer and *P. nebrodensis* (DC.:Fr.) Quel and the crossbreed between *P. eryngii* (DC.:Fr.) Quel. and *P. eryngii* (DC.:Fr.) Quel. var. *elaeoselini*, Table 4 shows their agronomic characteristics and morphological characteristics.

(1) The number of days in culture varied from 21 days to 36 days.
(2) The number of days in growth was from 10 days to 14 days.
(3) Morphological characteristics are various including colors and shapes close to those of the cap and stem of *P. ostreatus* (Jacq.: Fr.) Kummer, those expressing traits such as colors and shapes close to *P. eryngii* (DC.:Fr.) Quel., intermediate characteristics between *P. ostreatus* (Jacq.: Fr.) Kummer and *P. eryngii* (DC.:Fr.) Quel., and those closer to *P. nebrodensis* (DC.:Fr.) Quel. than to *P. ostreatus* (Jacq.: Fr.) Kummer or *P. eryngii* (DC.:Fr.) Quel. For colors, we referred to the RHS color chart.

TABLE 4

| Agronomic characteristics | Days in culture | 21 days to 36 days |
|---|---|---|
| | Days in growth | 10 days to 14 days |
| | Yielding ability | Yield: 20.3% to 31.6% |
| Morphological characteristics | Cap Shape | Funnel type, concave type, flat type, convex type |
| | Color | White, light yellow white, grayish blue, gray-brown, dark gray-brown, brown, dark brown, others (159C orange-white group, 22A yellow-orange group, etc.) |
| | Stem Shape | Thin and long, thin and short, thick and long, thick and short, thick in the middle |
| | Color | White, yellow white, light gray |
| Taste and flavor | Taste | Ones having strong sweetness, ones that do not have much taste and what not |
| | Food texture | Diversified including ones having food texture close to that of any one of *P. nebrodensis* (DC.:Fr.) Quel., *P. ostreatus* (Jacq.:Fr.) Kummer, *P. eryngii* (DC.:Fr.) Quel. and *P. eryngii* (DC.:Fr.) Quel. var. *elaeoselini* and one having food texture somewhere between any one of them. |

Next, the following describes practical strains obtained by repeating crossbreeding several times using *P. ostreatus* (Jacq.: Fr.) Kummer, *P. nebrodensis* (DC.:Fr.) Quel., *P. eryngii* (DC.:Fr.) Quel. and *P. eryngii* (DC.:Fr.) Quel. var. *elaeoselini*.

Example 5

Strains deposited in NITE (National Institute of Technology and Evaluation) Patent Microorganisms Depositary (NPMD), an independent administrative corporation, as NITE BP-1378 and NITE BP-1379 are those obtained by repeating the crossbreeding of monokaryotic hyphae by a dual culture, the monokaryotic hyphae being obtained by using *P. ostreatus* (Jacq.: Fr.) Kummer, *P. nebrodensis* (DC.:Fr.) Quel., *P. eryngii* (DC.:Fr.) Quel. and *P. eryngii* (DC.:Fr.) Quel. var. *elaeoselini* and performing single spore isolation from optionally-selected parent varieties. Specifically, it was performed as follows.

We obtained crossbreeds by crossbreeding *P. ostreatus* (Jacq.: Fr.) Kummer with *P. nebrodensis* (DC.:Fr.) Quel. and selected one variety after examining the shape, etc. (referred to as Crossbreed 1). On the other hand, we obtained crossbreeds by crossbreeding *P. eryngii* (DC.:Fr.) Quel. with *P. eryngii* (DC.:Fr.) Quel. var. *elaeoselini* and selected one variety after examining the shape, etc. (referred to as Crossbreed 2). Next, we obtained crossbreeds by crossbreeding Crossbreed 1 with Crossbreed 2 and selected one variety after examining the shape, etc. (referred to as Crossbreed 3). We obtained crossbreeds by crossbreeding Crossbreed 3 with *P. ostreatus* (Jacq.: Fr.) Kummer and selected one variety after examining the shape, etc. (referred to as Crossbreed 4). We obtained crossbreeds by crossbreeding Crossbreed 4 with *P. eryngii* (DC.:Fr.) Quel. and selected one variety after examining the shape, etc. (referred to as Crossbreed 5). We obtained crossbreeds by crossbreeding Crossbreed 5 with *P. ostreatus* (Jacq.: Fr.) Kummer and selected one variety after examining the shape, etc. (referred to as Crossbreed 6). We obtained crossbreeds by crossbreeding Crossbreed 5 with Crossbreed 6, examined the shape, etc., selected two strains from those crossbreeds and deposited those two strains in NITE (National Institute of Technology and Evaluation) Patent Microorganisms Depositary (NPMD), an independent administrative corporation, as Deposit Nos. NITE BP-1378 and NITE BP-1379.

Next, the following shows culturing examples on various agar media about various microbiological traits of each deposited strain.

We cultured each of Deposit No. NITE BP-1378 and Deposit No. NITE BP-1379 in advance on a potato dextrose agar medium, punched out 5.0 mm in diameter with a cork borer, inoculated each of the following media therewith and cultured in darkness.

Results of Deposit No. NITE BP-1378
(1) Growing Condition on Malt Extract Agar Medium (25° C.)

The diameter of a colony on the $6^{th}$ day was 23.5 mm, and the color of colony was white. The density of colony was very low and about the same compared with *P. eryngii* (DC.:Fr.) Quel. and *P. ostreatus* (Jacq.: Fr.) Kummer. The amount of aerial hyphae was small, slightly smaller than *P. eryngii* (DC.:Fr.) Quel. and about the same compared with *P. ostreatus* (Jacq.: Fr.) Kummer.

(2) Growing Condition on Potato Dextrose Agar Medium (25° C.)

The diameter of a colony on the $6^{th}$ day was 42.5 mm, and the color of colony was white. The density of colony was high and about the same compared with *P. eryngii* (DC.:Fr.) Quel. and *P. ostreatus* (Jacq.: Fr.) Kummer. The amount of aerial hyphae was large and slightly more compared with *P. eryngii* (DC.:Fr.) Quel. and *P. ostreatus* (Jacq.: Fr.) Kummer.

(3) Growing Condition on Sabouraud Agar Medium (25° C.)

The diameter of a colony on the $6^{th}$ day was 22.3 mm, and the color of colony was white. The density of colony was high and about the same compared with *P. eryngii* (DC.:Fr.) Quel. and *P. ostreatus* (Jacq.: Fr.) Kummer. The amount of aerial hyphae was large, about the same compared with *P. eryngii* (DC.:Fr.) Quel. and slightly more than *P. ostreatus* (Jacq.: Fr.) Kummer.

(4) Growing Condition on Synthetic Mucor Agar Medium (25° C.)

The diameter of a colony on the $6^{th}$ day was 17.1 mm, and the color of colony was white. The density of colony was high, about the same compared with *P. eryngii* (DC.:Fr.) Quel. and slightly higher than *P. ostreatus* (Jacq.: Fr.) Kummer. The amount of aerial hyphae was small, about the same compared with *P. eryngii* (DC.:Fr.) Quel. and slightly more than *P. ostreatus* (Jacq.: Fr.) Kummer.

(5) Growing Condition on YpSs Agar Medium (25° C.)

The diameter of a colony on the 6$^{th}$ day was 49.4 mm, and the color of colony was white. The density of colony was high and about the same compared with *P. eryngii* (DC.:Fr.) Quel. and *P. ostreatus* (Jacq.: Fr.) Kummer. The amount of aerial hyphae was moderate, about the same compared with *P. eryngii* (DC.:Fr.) Quel. and slightly less than *P. ostreatus* (Jacq.: Fr.) Kummer.

(6) Growing Condition on Czapk-Dox Agar Medium (25° C.)

The diameter of a colony on the 6$^{th}$ day was 32.9 mm, and the color of colony was white. The density of colony was very low, higher than *P. eryngii* (DC.:Fr.) Quel. and about the same compared with *P. ostreatus* (Jacq.: Fr.) Kummer. The amount of aerial hyphae was small and about the same compared with *P. eryngii* (DC.:Fr.) Quel. and *P. ostreatus* (Jacq.: Fr.) Kummer.

(7) Growing Condition on Oatmeal Agar Medium (25° C.)

The diameter of a colony on the 6$^{th}$ day was 59.2 mm, and the color of colony was white. The density of colony was high and about the same compared with *P. eryngii* (DC.:Fr.) Quel. and *P. ostreatus* (Jacq.: Fr.) Kummer. The amount of aerial hyphae was moderate, about the same compared with *P. eryngii* (DC.:Fr.) Quel. and less than *P. ostreatus* (Jacq.: Fr.) Kummer.

(8) Growing Condition on Phenoloxidase Assay Medium (25° C.)

On a potato dextrose medium added with 0.5% tannic acid, no hypha grew on the 6$^{th}$ day of culture, showing no root taking signs, and the color of the medium around the inoculum slightly changed to brown. Similar results were found in *P. eryngii* (DC.:Fr.) Quel. and *P. ostreatus* (Jacq.: Fr.) Kummer as well.

On a potato dextrose medium added with 0.5% gallic acid, no hypha grew on the 6$^{th}$ day of culture, and the color of portions around the inoculum changed to brown. When culture is continued thereafter, hyphae took root, and the diameter of a colony was 24.2 mm on the 9$^{th}$ day of inoculation. The color of colony was white. The density of colony was high and about the same compared with *P. eryngii* (DC.:Fr.) Quel. The amount of aerial hyphae was small and about the same compared with *P. eryngii* (DC.:Fr.) Quel. On the other hand, in *P. ostreatus* (Jacq.: Fr.) Kummer, neither root taking nor growth of hyphae was found and only the color of portions around the inoculum changed to brown.

(9) Optimum growth temperature: After inoculating a potato dextrose agar medium with a piece of hypha having a diameter of 5 mm and culturing at 25° C. for 2 days in advance, we cultured it at each temperature. When we measured the radius of the colony 6 days later, the optimum growth temperature was about 28° C. Moreover, hyphae hardly grew at 5° C. and growth was extremely poor at 34° C.

(10) Optimum growth pH: After sterilizing 25 mL of a PD liquid medium, we adjusted pH at 0.5 intervals aseptically with hydrochloric acid or potassium hydroxide in the range from pH3.0 to pH10.0. Subsequently, we inoculated it with a piece of hypha having a diameter of 5 mm, performed static culture for 15 days and then measured each dry weight to find that the optimum growth pH was about 6.0. Moreover, the growth of the present strain was well in the range from pH4.5 to pH9.0.

Results of Deposit No. NITE BP-1379

(1) Growing Condition on Malt Extract Agar Medium (25° C.)

The diameter of a colony on the 6$^{th}$ day was 49.0 mm, and the color of colony was white. The density of colony was very low and about the same as those of *P. eryngii* (DC.:Fr.) Quel. and *P. ostreatus* (Jacq.: Fr.) Kummer. The amount of aerial hyphae was small, slightly smaller than *P. eryngii* (DC.:Fr.) Quel. and about the same compared with *P. ostreatus* (Jacq.: Fr.) Kummer.

(2) Growing Condition on Potato Dextrose Agar Medium (25° C.)

The diameter of a colony on the 6$^{th}$ day was 61.2 mm, and the color of colony was white. The density of colony was high and about the same compared with *P. eryngii* (DC.:Fr.) Quel. and *P. ostreatus* (Jacq.: Fr.) Kummer. The amount of aerial hyphae was large and slightly more compared with *P. eryngii* (DC.:Fr.) Quel. and *P. ostreatus* (Jacq.: Fr.) Kummer.

(3) Growing Condition on Sabouraud Agar Medium (25° C.)

The diameter of a colony on the 6$^{th}$ day was 39.8 mm, and the color of colony was white. The density of colony was high and about the same compared with *P. eryngii* (DC.:Fr.) Quel. and *P. ostreatus* (Jacq.: Fr.) Kummer. The amount of aerial hyphae was large, about the same compared with *P. eryngii* (DC.:Fr.) Quel. and slightly more than *P. ostreatus* (Jacq.: Fr.) Kummer.

(4) Growing Condition on Synthetic Mucor Agar Medium (25° C.)

The diameter of a colony on the 6$^{th}$ day was 19.5 mm, and the color of colony was white. The density of colony was low, low compared with *P. eryngii* (DC.:Fr.) Quel. and about the same compared with *P. ostreatus* (Jacq.: Fr.) Kummer. The amount of aerial hyphae was moderate, more than *P. eryngii* (DC.:Fr.) Quel. and slightly less than *P. ostreatus* (Jacq.: Fr.) Kummer.

(5) Growing Condition on YpSs Agar Medium (25° C.)

The diameter of a colony on the 6$^{th}$ day was 63.5 mm, and the color of colony was white. The density of colony was high and about the same as those of *P. eryngii* (DC.:Fr.) Quel. and *P. ostreatus* (Jacq.: Fr.) Kummer. The amount of aerial hyphae was moderate, about the same compared with *P. eryngii* (DC.:Fr.) Quel. and slightly less than *P. ostreatus* (Jacq.: Fr.) Kummer.

(6) Growing Condition on Czapk-Dox Agar Medium (25° C.)

The diameter of a colony on the 6$^{th}$ day was 60.4 mm, and the color of colony was white. The density of colony was very low, higher than *P. eryngii* (DC.:Fr.) Quel. and about the same compared with *P. ostreatus* (Jacq.: Fr.) Kummer. The amount of aerial hyphae was small and about the same compared with *P. eryngii* (DC.:Fr.) Quel. and *P. ostreatus* (Jacq.: Fr.) Kummer.

(7) Growing Condition on Oatmeal Agar Medium (25° C.)

The diameter of a colony on the 6$^{th}$ day was 75.6 mm, and the color of colony was white. The density of colony was high and about the same as those of *P. eryngii* (DC.:Fr.) Quel. and *P. ostreatus* (Jacq.: Fr.) Kummer. The amount of aerial hyphae was moderate, about the same compared with *P. eryngii* (DC.:Fr.) Quel. and less than *P. ostreatus* (Jacq.: Fr.) Kummer.

(8) Growing Condition on Phenoloxidase Assay Medium (25° C.)

On a potato dextrose medium added with 0.5% tannic acid, no hypha grew on the 6$^{th}$ day of culture, showing no root taking signs, and the color of the medium around the inoculum slightly changed to brown. Similar results were found in *P. eryngii* (DC.:Fr.) Quel. and *P. ostreatus* (Jacq.: Fr.) Kummer as well.

On a potato dextrose medium added with 0.5% gallic acid, no hypha grew on the 6$^{th}$ day of culture, and the color of portions around the inoculum changed to brown. When culture is continued thereafter, hyphae took root, and the diameter of a colony was 8.0 mm on the 9$^{th}$ day of inoculation. The color of colony was white. The density of colony was high and about the same compared with *P. eryngii* (DC.:Fr.) Quel. The amount of aerial hyphae was small and about the same compared with *P. eryngii* (DC.:Fr.) Quel. On the other hand, in *P. ostreatus* (Jacq.: Fr.) Kummer, neither root taking nor growth of hyphae was found and only the color of portions around the inoculum changed to brown.

(9) Optimum growth temperature: After inoculating a potato dextrose agar medium with a piece of hypha having a diameter of 5 mm and culturing at 25° C. for 2 days in advance, we cultured it at each temperature. When we measured the radius of the colony 6 days later, the optimum growth temperature was about 28° C. Moreover, hyphae hardly grew at 5° C. and growth was extremely poor at 34° C.

(10) Optimum growth pH: After sterilizing 25 mL of a PD liquid medium, we adjusted pH at 0.5 intervals aseptically with hydrochloric acid or potassium hydroxide in the range from pH3.0 to pH10.0. Subsequently, we inoculated it with a piece of hypha having a diameter of 5 mm, performed static culture for 15 days and then measured each dry weight to find that the optimum growth pH was about 6.5. Moreover, the growth of the present strain was well in the range from pH4.5 to pH9.0.

Example 7

We had mushrooms germinate from Deposit No. NITE BP-1378 and Deposit No. NITE BP-1379 in a manner similar to the mushroom cultivation method in Example 2. Table 5 shows agronomic characteristics, morphological characteristics, etc. in the result of cultivation. The color of caps, the shape of stems, etc. are closer to those of *P. ostreatus* (Jacq.: Fr.) Kummer than to *P. eryngii* (DC.:Fr.) Quel. For colors, we referred to the RHS color chart.

Example 8

We examined the base sequence of each of *P. ostreatus* (Jacq.: Fr.) Kummer, *P. nebrodensis* (DC.:Fr.) Quel., *P. eryngii* (DC.:Fr.) Quel., *P. eryngii* (DC.:Fr.) Quel. var. *elaeoselini*, Deposit No. NITE BP-1378 as an interspecific hybrid and Deposit No. NITE BP-1379 as an interspecific hybrid in the internal transcription spacer region (hereinafter referred to as the ITS region) and compared them.

(1) Determination of Base Sequence in the ITS Region

From harvested and freeze-dried hyphae of six strains, i.e., *P. ostreatus* (Jacq.: Fr.) Kummer, *P. nebrodensis* (DC.: Fr.) Quel., *P. eryngii* (DC.:Fr.) Quel., *P. eryngii* (DC.:Fr.) Quel. var. *elaeoselini*, *P. nebrodensis* (DC.:Fr.) Quel., Deposit No. NITE BP-1378 and Deposit No. NITE BP-1379 which are incubated in a PDA plate medium, we respectively extracted DNA using a DNA extraction kit "Plant Geno-DNA-Template (TaKaRa Inc.)." We used each extracted DNA as a template and ITS1 (5'-TCCGTAGGTGAACCT-GCGG) (SEQ ID NO. 7) and ITS4 (5'-TCCTCCGCTTAT-TGATATGC) (SEQ ID NO. 8) as a pair of primers to amplify the ITS region of a ribosomal DNA by a PCR (Polymerase Chain Reaction) method, purified a PCR product thus obtained and then determined a base sequence by sequencing. We made a request to Bex Co., Ltd. for performing sequencing by a dye-terminator method using ABI Prism 3130 Genetic Analyzer (Applied Biosystems Japan).

(2) Analysis of Genetic Characteristics

Based on the base sequence in the ITS region of each of the abovementioned six strains, we calculated an evolutionary distance with the kimura 2-parameter using a MEGA (5.05) program, wherein the FIGURE shows molecular evolutionary relationships by the UPGMA method. In this case, we set the boot-strapping value to 1000.

Based on the results, we performed final identification of mushrooms used in the present examples to find that NITE BP-1378 was highly homologous to the sequence of "*P.*

TABLE 51

| | | | NITE BP-1378 | NITE BP-1379 |
|---|---|---|---|---|
| Agronomic characteristics | Days in culture | | 21 days | 21 days |
| | Days in growth | | 12 days | 12 days |
| | Yielding ability | | Yield 31.6% | Yield 31.6% |
| Morphological characteristics | Cap | Shape | Convex type and edges are rolled up inward. When matured, the center portion of caps is slightly dented and rolling-up on the edge is weakened. Surface is smooth. | Flat type and edges are rolled up inward. When matured, the center portion of caps is slightly dented and rolling-up on the edge is weakened. Surface is smooth. |
| | | Size | 30 mm to 40 mm | 35 mm to 45 mm |
| | | Color | Gray-brown (N199A, gray-brown group) | Gray-brown (N199B, gray-brown group), thin fibrous patterns are observed. |
| | Stem | Size Shape color | Cylindrical type of 65-75 mm × 8-9 mm White (155D, white-group) Surface is smooth and interior is solid. | Cylindrical type of 60-65 mm × 8-10 mm White (155D, white-group) Surface is smooth and interior is solid. |
| | Lamellae | | Decurrent on the stem and tip end is smooth. Grayed white (156B, grayed white group) | Decurrent on the stem and tip end is smooth. Grayed white (156A, grayed white group) |
| | Basidium | Shape Size | Long club-shaped, 4-spore type 23-27 μm × 6-9 μm | Long club-shaped, 4-spore type 24-27 μm × 5-7 μm |
| | Basidiospore | Shape Size Color of spore print | Cylindrical type 9.0-11.0 μm × 3.5-5.0 μm White | Cylindrical type 6.5-10.5 μm × 2.5-4.5 μm White |
| | Cheilocystidium | Shape Size | Club shaped 18.0-22.0 μm × 4.5-7.0 μm | Club shaped 19.0-23.0 μm × 4.0-7.0 μm |
| Taste, flavor | Taste | | Unique taste and flavor | Unique taste and flavor |
| | Food texture | | Moderate hardness, crispy | Moderate hardness, crispy |

*eryngii* (DC.:Fr.) Quel.," a mushroom of *Pleurotus* spp. and that NITE BP-1379 was highly homologous to both sequences of "*P. eryngii*" and "*P. ostreatus*." This result has established that NITE BP-1379 has both genes of *P. ostreatus* (Jacq.: Fr.) Kummer and *P. eryngii* (DC.:Fr.) Quel. On the other hand, NITE BP-1378 is close to *P. eryngii* (DC.: Fr.) Quel. in the ITS region, but the shape of mushrooms is close to *P. ostreatus* (Jacq.: Fr.) Kummer than to *P. eryngii* (DC.:Fr.) Quel. based on the result of Example 7, and therefore we have determined in view of total consideration that it has mixed traits of *P. ostreatus* (Jacq.: Fr.) Kummer and *P. eryngii* (DC.:Fr.) Quel.

INDUSTRIAL FIELD OF APPLICATION

The present invention is useful in producing and providing novel species of mushrooms, providing processed goods using novel species of mushrooms, providing menus using novel species of mushrooms, among others, in the fields of agriculture and foods.

DEPOSIT NUMBER

MH006403 NITE BP-1378
MH006404 NITE BP-1379

What is claimed is:

1. *Pleurotus* interspecific hybrid NITE BP-1378 or NITE BP-1379, representative inoculum having been deposited at the National Institute of Technology and Evaluation, Patent Microorganism Depository, obtained by using *P. ostreatus* (Jacq.: Fr.) Kummer, *P. nebrodensis* (DC.:Fr.) Quel., *P. eryngii* (DC.:Fr.) Quel. or *P. eryngii* (DC.:Fr.) Quel. var. *elaeoselini* respectively as parents.

2. A method for cultivating an interspecific hybrid of *Pleurotus* spp., comprising generating *Pleurotus* interspecific hybrid NITE BP-1378 or NITE BP-1379, representative inoculum having been deposited at the National Institute of Technology and Evaluation, Patent Microorganism Depository, by inoculating a mushroom cultivation medium therewith.

* * * * *

SEQUENCE LISTING

```
<160> NUMBER OF SEQ ID NOS: 8

<210> SEQ ID NO 1
<211> LENGTH: 572
<212> TYPE: DNA
<213> ORGANISM: Pleurotus ostreatus  (Jacq.:Fr.) Kummer

<400> SEQUENCE: 1
ttgttgctgg cctctagggg catgtgcacg cttcactagt ctttcacccc tgtgaacttt      60
tgatagatct gtgaagtcgt ctttcaagtc gtcagacttg gtttgctggg atttaaacgt     120
ctcggtgtga caacgcagtc tatttactta acacacccca aatgtatgtc tacgaatgtc     180
atttaatggg ccttgtgcct ataaaccata atacaacttt caacaacgga tctcttggct     240
ctcgcatcga tgaagaacgc agcgaaatgc gataagtaat gtgaattgca gaattcagtg     300
aatcatcgaa tctttgaacg cacccttgcgc cccttggtat tccgaggggc atgcctgttt     360
gagtgtcatt aaattctcaa actcactttg gttttttcca attgtgatgt ttggattgtt     420
gggggctgct ggccttgaca ggtcggctcc tcttaaatgc attagcagga cttctcattg     480
cctctgcgca tgatgtgata attatcactc atcaatagca cgcagaatag agtccagctc     540
tctaatcgtc cgcaaggaca attgacaatt ga                                  572

<210> SEQ ID NO 2
<211> LENGTH: 629
<212> TYPE: DNA
<213> ORGANISM: Pleurotus eryngii (DC.:Fr.) Quel. ver. nebrodensis
      Inzenga

<400> SEQUENCE: 2
ttgttgctgg cctctagggg catgtgcacg cttcactagt ctttcaaccc ctgtgaactt      60 tgatagatc tgtgaagtcg tctctcaagt cgtcagactt ggtttgctgg gatttaaatg     120
tcttagtgtg actacgcagt ctatttactt atacaccccc aaatgtatgt ctacgaatgt     180
catttaatgg gccttgtgcc tataaaccat aatacaactt tcaacaacgg atctcttggc     240
tctcgcatcg atgaagaacg cagcgaaatg cgataagtaa tgtgaattgc agaattcagt     300
gaatcatcga atctttgaac gcaccttgcg ccccttggta ttccgagggg catgcctgtt     360
tgagtgtcat taaattctca aactcactct ggttttttcca attgtgatgt ttggattgtt     420
gggggctgct ggccttgaca ggtcggctcc tcttaaatgc attagcagga cttctcattg     480
cctctgcgca tgatgtgata attatcactc atcaatagca cgcatgaata gagtctggct     540
ttctaaccgt ccgcaaggac aatttgacaa tttgacctca aatcaggtag gactacccgc     600
tgaacttaag catatcaata agcggagga                                      629
```

<210> SEQ ID NO 3
<211> LENGTH: 555
<212> TYPE: DNA
<213> ORGANISM: Pleurotus eryngii (DC.:Fr.) Quel

<400> SEQUENCE: 3

```
ttgttgctgg cctctagggg catgtgcacg cttcactagt ctttcacccc tgtgaacttt      60
tgatagatct gtgaagtcgt ctctcaagtc gttagacttg gtttgctggg atgtaaacgt     120
ctcggtgtga ctacgcagtc tatttactta taacacccca aatgtatgtc tacgaatgtc     180
atttaaaggg ccttgtgcct ataaaccata atacaacttt caacaacgga tctcttggct     240
ctcgcatcga tgaagaacgc agcgaaatgc gataagtaat gtgaattgca gaattcagtg     300
aatcatcgaa tctttgaacg caccttgcgc cccttggtat tccgagggge atgcctgttt     360
gagtgtcatt aaattctcaa actcactctg ttttttccaa ttgtgatgtt tggattgttg     420
ggggctgctg gccttgacag gtcggctcct cttaaatgca ttagcaggac ttctcattgc     480
ctctgcgcat gatgtgataa ctatcactca tcaatagcac gcatgaatag agtttggctc     540
tctaaccgtc cgcaa                                                      555
```

<210> SEQ ID NO 4
<211> LENGTH: 605
<212> TYPE: DNA
<213> ORGANISM: Pleurotus eryngii (DC.:Fr.) var. elaeoselini

<400> SEQUENCE: 4

```
ttgttgctgg cctctagggg catgtgcacg cttcactagt ctttcaaccc ctgtgaactt      60
ttgatagatc tgtgaagtcg tctctcaagt cgttagactt ggtttgctgg gatgtaaacg     120
tctcggtgtg actacgcagt ctatttactt ataacacccc aaatgtatgt ctacgaatgt     180
catttaaagg gccttgtgcc tataaatcat aatacaactt tcaacaacgg atctcttggc     240
tctcgcatcg atgaagaacg cagcgaaatg cgataagtaa tgtgaattgc agaattcagt     300
gaatcatcga atctttgaac gcaccttgcg ccccttggta ttccgagggg catgcctgtt     360
tgagtgtcat taaattctca actcactctg gttttttcca attgtgatgt ttggattgtt     420
gggggctgct ggccttgaca ggtcggctcc tcttaaatgc attagcagga cttctcattg     480
cctctgcgca tgatgtgata attatcactc atcaatagca cgcatgaata gagtctggct     540
ctctaaccgt ccgcgaggac aatttgacaa tttgacctca aatcaggtag gactacccgc     600
tgaac                                                                 605
```

<210> SEQ ID NO 5
<211> LENGTH: 584
<212> TYPE: DNA
<213> ORGANISM: Pleurotus sp. NITE P-1378

<400> SEQUENCE: 5

```
ttgttgctgg cctctagggg aatgtgcacg cttcactagt ctttcacccc tgtgaacttt      60
tgatagatct gtgaagtcgt ctctcaagtc gttagacttg gtttgctggg atgtaaacgt     120
ctcggtgtga ctacgcagtc tatttactta taacacccca aatgtatgtc tacgaatgtc     180
atttaaaggg ccttgtgcct ataaaccata atacaacttt caacaacgga tctcttggct     240
ctcgcatcga tgaagaacgc agcgaaatgc gataagtaat gtgaattgca gaattcagtg     300
aatcatcgaa tctttgaacg caccttgcgc cccttggtat tccgagggge atgcctgttt     360
```

```
gagtgtcatt aaattctcaa actcactctg gtttttccaa ttgtgatgtt tggattgttg      420
ggggctgctg gccttgacag gtcggctcct cttaaatgca ttagcaggac ttctcattgc      480
ctctgcgcat gatgtgataa ctatcactca tcaatagcac gcataaatag agtctggctc      540
tctaaccgtc cgcaaggaca attgacaatt gactcaatca ggta                       584

<210> SEQ ID NO 6
<211> LENGTH: 566
<212> TYPE: DNA
<213> ORGANISM: Pleurotus sp. NITE P-1379

<400> SEQUENCE: 6
ttgttgctgg cctctagggg catgtgcacg cttcactagt ctttcacccc tgtgaacttt       60
tgatagatct gtgaagtcgt ctytcaagtc gtyagacttg gtttgctggg atktaaacgt      120
ctcggtgtga cwacgcagtc tatttactta wmacacccca aatgtatgtc tacgaatgtc      180
atttaawggg ccttgtgcct ataaaccata atacaacttt caacaacgga tctcttggct      240
ctcgcatcga tgaagaacgc agcgaaatgc gataagtaat gtgaattgca gaattcagtg      300
aatcatcgaa tctttgaacg caccttgcgc cccttggtat tccgaggggc atgcctgttt      360
gagtgtcatt aaattctcaa actcactytg gtttttccca attgtgatgt ttggattgtt      420 ggggggctgct ggccttgaca ggtcggctcc tcttaaatgc attagcagga cttctcattg      480
cctctgcgca tgatgtgata aytatcactc atcaatagca cgcakaatag agtccrgctc      540
tctaaycgtc cgcaaggaca attgac                                           566

<210> SEQ ID NO 7
<211> LENGTH: 19
<212> TYPE: DNA
<213> ORGANISM: Artificial Sequence
<220> FEATURE:
<223> OTHER INFORMATION: Primer name "ITS1"

<400> SEQUENCE: 7
tccgtaggtg aacctgcgg                                                    19

<210> SEQ ID NO 8
<211> LENGTH: 20
<212> TYPE: DNA
<213> ORGANISM: Artificial Sequence
<220> FEATURE:
<223> OTHER INFORMATION: Primer name "ITS4"

<400> SEQUENCE: 8
tcctccgctt attgatatgc                                                   20
```